United States Patent
Walter et al.

(10) Patent No.: US 9,156,767 B2
(45) Date of Patent: Oct. 13, 2015

(54) METHOD FOR THE PRODUCTION OF NOBLE METAL OXALATE COMPLEXES

(71) Applicant: Heraeus Precious Metals GmbH & Co. KG, Hanau (DE)

(72) Inventors: Richard Walter, Alzenau (DE); Florian Eweiner, Hanau (DE); Walter Låssig, Gelnhausen (DE); Jörg Fuchs Alameda, Biebergemünd (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 14/432,224

(22) PCT Filed: Sep. 24, 2013

(86) PCT No.: PCT/EP2013/069787
§ 371 (c)(1),
(2) Date: Mar. 30, 2015

(87) PCT Pub. No.: WO2014/053351
PCT Pub. Date: Apr. 10, 2014

(65) Prior Publication Data
US 2015/0232405 A1    Aug. 20, 2015

Related U.S. Application Data

(60) Provisional application No. 61/710,226, filed on Oct. 5, 2012.

(30) Foreign Application Priority Data

Oct. 5, 2012   (DE) .......................... 10 2012 019 560

(51) Int. Cl.
C07C 51/14    (2006.01)
C07C 51/41    (2006.01)

(52) U.S. Cl.
CPC ................................... *C07C 51/418* (2013.01)

(58) Field of Classification Search
None
See application file for complete search history.

(56) References Cited

FOREIGN PATENT DOCUMENTS

EP    0254935    *    2/1988
EP    0254935 A1    2/1988

OTHER PUBLICATIONS

Database Reaxys [Online] Abstract, Bi Si Kalova: Ukr. Khim. Zh., vol. 17, 1951, pp. 807-814.*
Database Reaxys [Online] Abstract, Justus Liebigs Annalen der Chemie, vol. 102, Jan. 1, 1857, pp. 41-54.*
Database Reaxys [Online] Abstract, Ber. Dtsch. Chem. Ges., vol. 35, Jan. 1, 1902, pp. 483-492.*

(Continued)

*Primary Examiner* — Karl J Puttlitz
(74) *Attorney, Agent, or Firm* — Panitch Schwarze Belisario & Nadel LLP

(57) ABSTRACT

The production of noble metal oxalate complexes from noble metal precursors and oxalic acid and/or oxalic acid salts is an exothermic reaction, in which heat and $CO_2$ are produced, is described. The temperature can increase above the decomposition point of the noble metal oxalate complexes in the course of the reaction, which simultaneously releases more $CO_2$. For safety reasons, when the reaction is carried out on a large scale, it is therefore necessary to take into consideration that the product must not be decomposed by heat that is produced during the reaction. Therefore, according to the invention, a method for the production of noble metal oxalate complexes is provided, in which the product noble metal oxalate complexes are added to the reaction mixture as an auto-catalyst.

13 Claims, 1 Drawing Sheet

(56) References Cited

OTHER PUBLICATIONS

Chen et al., Res Chem Intermed (2012) 38:421-428.*

Int'l Search Report issued Jan. 27, 2014 in Int'l Application No. PCT/EP2013/069787.

Kohlschuetter, "Ueber Doppelsalze des Cadmiurns und Quecksilbers," Ber. Dtsch. Chem. Ges., vol. 35, pp. 483-492 (1902); Abstract only.

Souchay et al, "Ueher die Oxalate der Schweren Metalloxyde," Justus Liebigs Annalen der Chemie, vol. 102, pp. 41-54 (1857); Abstract only.

Bisikalova, Ukr. Khim. Zh., vol. 17, pp. 807-814 (1951); Abstract only.

Krogmann et al, "Über die 'Isomerie' der Dioxalatoplatinate 2. Die freien Säuren," Chemische Berichte, vol. 99, No. 11, pp. 3408-3418 (Nov. 1966).

Sano, "On the Catalytic Decomposition of Oxalic Acid by Colloidal Platinum," Bulletin, vol. 15, No. 5, pp. 196-204 (1940).

Szabo et al, "Kinetik der thermischen Zersetzung von Silberoxalat," Zeitschrift fuer Elektrochemic, vol. 50, No. 8, pp. 869-874 (1956).

* cited by examiner

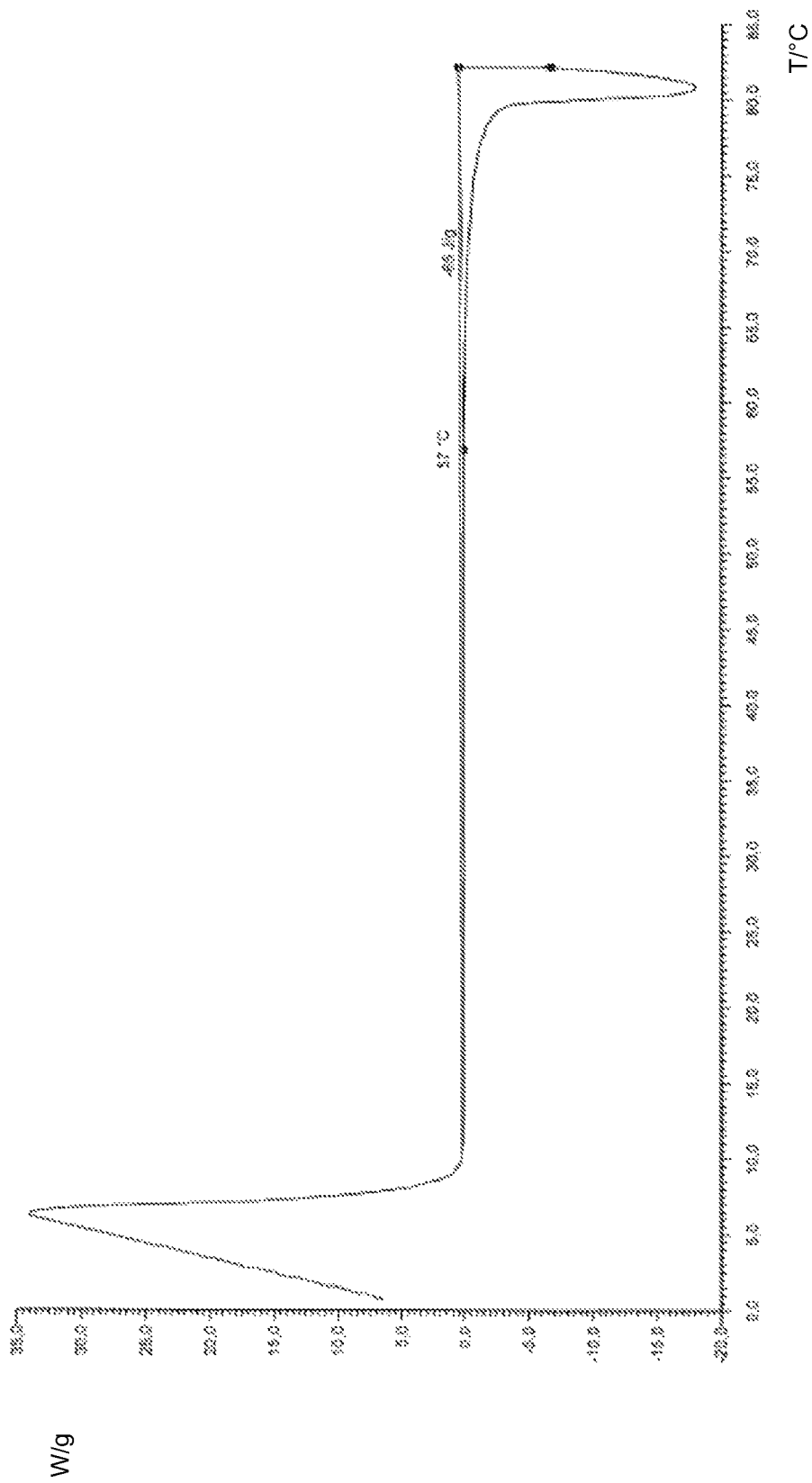

METHOD FOR THE PRODUCTION OF NOBLE METAL OXALATE COMPLEXES

CROSS-REFERENCE TO RELATED APPLICATIONS

This application is a Section 371 of International Application No. PCT/EP2013/069787, filed Sep. 24, 2013, which was published in the German language on Apr. 10, 2014 under International Publication No. WO 2014/053351 A1, which claims the benefit of U.S. Provisional Application No. 61/710,226, filed Oct. 5, 2012, the disclosures of which are incorporated herein by reference.

BACKGROUND OF THE INVENTION

The present invention relates to the production of noble metal oxalate complexes. Hereinafter, noble metal oxalate complexes shall also be referred to as noble metal oxalates for reasons of simplicity. Specifically, the invention relates to the production of noble metal oxalate complexes from noble metal precursors and oxalic acid and/or oxalic acid salts.

The production of noble metal oxalate complexes from noble metal precursors and oxalic acid and/or oxalic acid salts has been known for a long time. The production of platinum oxalate complexes usually proceeds through the reaction of platinum oxide hydrate (platinum(IV)-hydroxoacid, dihydrogenhexahydroxoplatinate(IV), hydroxoplatinic acid) and oxalic acid at a temperature of 60° C. (K. Krogmann, P. Dodel, *Chem. Ber.* 99, 3408-3418 (1966)).

EP 0 254 935 A1 describes a method for the production of silver oxalate having a large particle diameter. According to this method, silver salt and oxalic acid or oxalic acid salts are reacted at a pH value of no more than 5. The reaction is carried out at a temperature from 0 to 80° C., preferably at a temperature from 40 to 60° C.

The production of noble metal oxalate complexes from noble metal precursors and oxalic acid and/or oxalic acid salts is an exothermic reaction, in which heat and $CO_2$ are produced. The temperature can increase above the decomposition point of the noble metal oxalate complexes in the course of the reaction, which simultaneously releases more $CO_2$. In this context, see, for example, Sano, Isamu; *Bulletin*; 15, p. 196, "On the Catalytic Decomposition of Oxalic Acid by Colloidal Platinum" (1940), and Szabó, Z. G. and Biro-Sugar, E., *Zeitschrift für Elektrochemie*, vol. 50, no. 8, p. 869-874, "Kinetik der thermischen Zersetzung von Silberoxalat" (1956).

For safety reasons, when the reaction is carried out on a large scale, it is therefore necessary to take into consideration that the product must not be decomposed by heat that is produced during the reaction.

BRIEF SUMMARY OF THE INVENTION

It is therefore the object of the present invention to provide a method for the production of noble metal oxalate complexes that can be carried out on a large scale. Accordingly, the method enables the course of the reaction to be controlled. It is necessary that the amounts of gas and heat produced during the synthesis can be reliably guided away from the reactor.

These objectives are met by a method for the production of noble metal oxalate complexes which comprises reacting a noble metal precursor with oxalic acid and/or oxalic acid salt, wherein the product noble metal oxalate complexes are also added to the reaction as an auto-catalyst.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawing:

FIG. 1 is a graph of heat flow as a function of temperature for a platinum oxalate solution.

DETAILED DESCRIPTION OF THE INVENTION

The invention provides a method for the production of noble metal oxalate complexes, in which noble metal precursors are reacted with oxalic acid and/or oxalic acid salts, and in which noble metal oxalate is introduced into the reaction mixture as an auto-catalyst.

According to the invention, noble metal precursors and oxalic acid and/or oxalic acid salts are used as reactants. Many starting substances are conceivable, whereby the noble metal precursor and oxalic acid and/or oxalic acid salt reactants are obviously different from the noble metal oxalate end-product.

The term "noble metal" includes, in particular, the classical noble metals Pt, Pd, Ir, Rh, Os, Ru, Ag, and Au, and also the semi-noble metal Re. Preferred noble metals include silver, palladium, and platinum; platinum is particularly preferred.

Examples of noble metal precursors include noble metal salts and noble metal oxide hydrates. Examples of noble metal salts include noble metal nitrates, noble metal acetates, and mixtures thereof. It is also conceivable to use mixtures of a noble metal oxide hydrate and noble metal salt or salts. However, noble metal oxide hydrate, in particular platinum oxide hydrate, also referred to as platinum(IV) hydroxoacid (see Gmelin, *Verlag Chemie GmbH*, Berlin p. 47-48 (1940)) has proven to be preferred. The salt which is used also depends on the type of noble metal. For example, silver oxalate can be produced from silver nitrate, and it is preferable to use platinum-(IV) hydroxoacid or any of the salts thereof, such as $K_2Pt(OH)_6$, $Na_2Pt(OH)_6$ etc., as starting materials for platinum oxalate. As a matter of rule, the free acid is preferred.

Oxalic acid salts may include, for example, sodium oxalate, ammonium oxalate, potassium oxalate or mixtures thereof. However, it is also feasible to use a mixture of oxalic acid and one or more oxalic acid salt(s). As before, the preferred reactants depend on the type of noble metal. Accordingly, e.g., ammonium oxalate can be used to advantage for the production of silver oxalate. However, as a matter of rule, the use of free oxalic acid is particularly preferred. Accordingly, it is also preferable to use oxalic acid for the production of platinum oxalate.

According to the invention, a combination of noble metal oxide hydrate and oxalic acid reactants is particularly preferred because only carbon dioxide and water are produced in addition to the noble metal oxalate complexes.

It is particularly preferred to add the oxalic acid or oxalic acid salt at a suitable stoichiometric ratio. Referring to the production of platinum oxalate complexes, this means that 1.8 to 2.8 molar equivalents of oxalic acid or oxalic acid salt relative to platinum in the form of the platinum precursor are added. This reaction produces a mixture of different dioxalatoplatinic acids or platinum oxalate complexes. A detailed description of mixtures of this type is in K. Krogmann, P. Dodel, *Chem. Ber.* 99, pp. 3402-3407 and 3408-3418 (1966).

The form in which the oxalic acid and/or oxalic acid salt is added depends on the noble metal oxalate complex to be produced. Preferably, it is added in the form of an aqueous solution or as a solid. Oxalic acid is preferred and is preferably added as a solid in the form of oxalic acid dihydrate.

The reaction is carried out at a temperature below the decomposition temperature of the noble metal oxalate complexes. For defining the safety margin for the reaction temperature in the present case, a hazard evaluation needs to be considered which takes into account important parameters of process technology, parameters of equipment technology, and considerations and data of safety technology, such as, e.g., the decomposition temperature or decomposition range of the noble metal oxalate complexes. The reaction temperature may then be adjusted to come close to the decomposition temperature as a function of the existing data.

The reaction is therefore preferably performed at a temperature below the decomposition temperature of the noble metal oxalate complexes. In this context, the difference between reaction temperature and decomposition temperature should be at least 1° C., preferably at least 5° C. The decomposition temperature is defined to be the temperature at which decomposition starts, in which the start of decomposition is determined using long-term differential thermal analysis in glass ampules at a heating rate of 0.05 K/min in accordance with DIN 51007. Proven to be preferred for the reaction of noble metal precursors and oxalic acid and/or oxalic acid salts is a temperature range between 0° C. and 56° C., particularly preferably between 30° C. and 52° C., and even more particularly preferably between 35° C. and 45° C.

Referring, in particular, to platinum oxalate complexes already decomposing at a temperature of 57° C. (see FIG. 1), it is preferable to carry out the reaction at a temperature of up to 56° C., particularly preferably at up to 52° C., and even more particularly preferably at up to 45° C. The reaction is carried out above 0° C., preferably above 30° C., and particularly preferably at a temperature of 35° C. to 42° C.

According to the invention, the decomposition temperature of the noble metal oxalate complexes is determined by long-term differential thermal analysis (DTA) in accordance with DIN 51007 (June 1994). The determination can be done on solutions of noble metal oxalate complexes that correspond to the product solution, in a closed glass ampule at a heating rate of 0.05 K/min between 0° C. and a temperature above the measured peak trough (see FIG. 1). According to the invention, the decomposition temperature shall be understood to be the temperature when the first deviation (see FIG. 1, 57° C.) of the measuring curve from the starting baseline curve is noted (5.2 DIN 51007).

In the present case, 2934.5 mg of a 10% by weight platinum oxalate solution in water were used. The measurement proceeded in glass ampules at a heating rate of 0.05 K/min. FIG. 1 shows the heat flow W/g as a function of the temperature between 2° C. and 83° C.

In the present description, temperature-equilibrate shall be understood to mean that the reaction mixture is set to a certain temperature. The temperature equilibration can be effected, e.g., with water.

It is advantageous to first produce an aqueous solution or suspension of noble metal oxide hydrate or noble metal salt. Referring to the production of platinum oxalate complexes, it is preferred to first produce an aqueous suspension of platinum oxide hydrate ($H_2[Pt(OH)_6]$ or platinum-(IV) hydroxoacid). It is preferable to produce a 5 to 25% by weight suspension, particularly preferably a 7-15% by weight suspension relative to platinum in water.

Surprisingly, it has been found that the introduction of small amounts of noble metal oxalate complexes into the reaction mixture has an auto-catalytic effect. The addition of noble metal oxalate complexes significantly shortens the induction period of the reaction (very slow starting phase of the reaction). This enables the course of the reaction to be controlled. Therefore, the added noble metal oxalate complexes are also referred to as auto-catalysts hereinafter. According to the invention, a small amount of auto-catalyst is added. Preferably, the amount of auto-catalyst to be added is $1 \times 10^{-4}$ to $5 \times 10^{-2}$ molar equivalents of noble metal relative to the noble metal in the noble metal precursor. Particularly preferably, the amount of auto-catalyst to be added is $5 \times 10^{-4}$ to $1 \times 10^{-2}$ molar equivalents of noble metal relative to the noble metal in the noble metal precursor, and particularly preferably the amount of auto-catalyst to be added is $5 \times 10^{-4}$ to $7 \times 10^{-3}$ molar equivalents of noble metal relative to the noble metal in the noble metal precursor. It is preferable to add the auto-catalyst in aqueous solution. Customary concentrations are 5-20% by weight, e.g. 8-15% by weight.

Expediently, the noble metal oxalate complexes corresponding to the product to be produced are used as auto-catalyst (in line with the meaning of the term, "auto-catalyst"). This means that platinum oxalate is used as an auto-catalyst for the production of platinum oxalate and silver oxalate is used as an auto-catalyst for the production of silver oxalate, etc.

The order in which the noble metal precursor, auto-catalyst, and oxalic acid and/or oxalic acid salt are added is less important. The auto-catalyst may be added to the reaction solution or suspension concurrently with the total amount of oxalic acid and/or oxalic acid salt, concurrently with part of the oxalic acid and/or oxalic acid salt, or before the addition of oxalic acid and/or oxalic acid salt. A solution or a suspension of noble metal precursor may be provided first or added later in this context.

If the noble metal precursor is provided first and the auto-catalyst and oxalic acid are added concurrently, the addition should be made at a temperature below the desired reaction temperature. The addition is preferably made at a temperature of up to 37° C., particularly preferably at up to 32° C. The reaction mixture thus formed is then heated up to the desired reaction temperature. The heating rate is then a function of when the reaction starts.

However, it has proven to be advantageous to first provide the noble metal precursor in solution or suspension, then add the auto-catalyst, and to add at least the major part of the oxalic acid or oxalic acid salt only after the reaction temperature is reached.

The oxalic acid or the oxalic acid salt may be added in one or more aliquots. The aliquots may be equal in size, or multiple aliquots differing in size may just as well be added. If the aliquots differ in size, it is advantageous to first add a larger aliquot and then add one or more smaller aliquots or progressively smaller aliquots. Accordingly, it has proven to be advantageous to first add an aliquot of 0.4 to 1.4 molar equivalents relative to platinum in the form of the platinum precursor and to subsequently add, e.g., multiple equal amounts of the remaining oxalic acid or the remaining oxalic acid salt. This can be done, for example, in a single further addition of e.g., 0.4 to 1.4 molar equivalents, in two further additions of, e.g., 0.2 to 0.9 molar equivalents, in three further additions of, e.g., 0.1 to 0.7 molar equivalents, in four further additions of, e.g., 0.1 to 0.6 molar equivalents, etc. However, it is just as conceivable to add the oxalic acid or the oxalic acid salt evenly and continuously.

It is advantageous to stir the solution or suspension during the reaction. In a preferred embodiment, the oxalic acid or the oxalic acid salt is added as a function of the stirring conditions, concentration of the solution or suspension, and reactor dimensions. As a matter of principle, the rate at which oxalic acid or oxalic acid salt can be added may be set quite well based on the production of $CO_2$ and on the temperature profile.

Noble metal oxalate complexes produced as specified above may advantageously be used as precursors for noble metal catalysts.

EXAMPLES

The following examples serve purposes of illustration and are not to be construed as to limit the invention.
Measuring Method and Analyses NMR and UV spectroscopy were used in the qualitative analyses. The UV spectrum was measured at room temperature using a Specord® 200 UV spectrometer made by Analytic Jena AG and 1 cm cuvettes (QS Suprasil® quartz glass cuvettes made by Heraeus Quarzglas GmbH) over a measuring range from 190 nm-1,100 nm at a resolution of 2 nm. The nuclear resonance spectroscopic measurements were carried out using a Bruker Avance 400 MHz NMR spectrometer (Reference Example 1) and a Bruker Avance 600 MHz NMR spectrometer (Example, Reference Examples 2 and 3).

The platinum content was determined by gravimetry.

The reactants used were platinum (IV) hydroxoacid ($H_2[Pt(OH)_6]$) from in-house production (wt (Pt): 55.51%), oxalic acid dihydrate for analysis EMSURE® ACS, ISO, Reag. Ph Eur made by Merck KGaA, art. no. 100495, and platinum oxalate from in-house production (wt (Pt): 11.72%).

Example 1

Production of Platinum Oxalate at 40° C., in the Presence of Auto-Catalyst, Oxalic Acid Added in 5 Aliquots A total of 10 g Pt (50 mmol) in the form of 18.01 g $H_2[Pt(OH)_6]$ were placed in 54.29 ml demineralized water ("VEW") in a 250 ml three-necked round flask. Then, 0.04 g Pt oxalate (0.24 mmol Pt) were added as an auto-catalyst at room temperature (23° C.) while stirring (250 U/min) with a magnetic stirrer. A pale-greenish suspension was thus produced.

Time: 0 min: The suspension was heated in a water bath from room temperature to 40° C. over the course of 20 minutes.

Time 20 min: As soon as the temperature of the suspension had reached 40° C., one of five equal aliquots of 2.568 g (20 mmol) oxalic acid dihydrate was added. Instantaneously gas production was observed, which lasted for a period of 60 minutes. A total of 270 ml $CO_2$ were captured.

Time 80 min: Once gas production ceased, another aliquot of 2.568 g (20 mmol) oxalic acid dihydrate was added. A total of 40 ml $CO_2$ were captured.

Time 140 min: Once gas production ceased, another aliquot of 2.568 g (20 mmol) oxalic acid dihydrate was added. The color of the solution changed from green to turquoise-blue after 10 min. A total of 300 ml $CO_2$ were captured over the course of 60 min.

Time 200 min: Once gas production ceased, another aliquot of 2.568 g (20 mmol) oxalic acid dihydrate was added. A total of 270 ml $CO_2$ were captured over the course of 60 min.

Time 260 min: Once gas production ceased, another aliquot of 2.568 g (20 mmol) oxalic acid dihydrate was added. A total of 300 ml $CO_2$ were captured over the course of 110 min. No further gas production was observed during 10 more minutes of stirring at 40° C.

Time 380 min: The heating system was switched off and the solution was stirred until room temperature was reached. The mixture was filtered through a 0.2 μm membrane filter (Sartorius filtration unit). Filtration was carried out within 30 minutes.

A total of 74.49 g of product having a Pt content of 13.40% by weight were obtained with the yield being 99.82% relative to platinum. $^{13}$C-NMR (151 MHz, 299.6 K, DMSO-$d_6$ capillary): δ=168.70; 167.16 ppm. UV-VIS: 627 nm (A=0.399); 417 nm (0.415).

Reference Example 1

Production of Platinum Oxalate at 50° C.

A total of 10 g Pt (50 mmol) in the form of 18.01 g $H_2[Pt(OH)_6]$ were placed in 54.29 ml demineralized water ("VEW") in a 250 ml three-necked round flask. Then, 12.93 g (100 mmol) oxalic acid dihydrate were added while stirring (250 U/min) with a magnetic stirrer. A milky, yellowish-white suspension was thus produced.

Time: 0 min: The suspension was heated in a water bath at a rate of approx. 1° C./10 min starting at 19° C.

Time 180 min: The solution started to turn greenish at a temperature of 35° C.

Time 210 min: The solution turned turquoise-blue at a temperature of 38° C.

Time 220 min: The solution turned deep-blue at a temperature of 39° C.

Time 230 min: The temperature of the solution reached 40° C. Gas production was for a period of 50 min, during which the temperature of the solution reached 45° C.

Time 350 min: The temperature reached 50° C. There was no longer any gas production.

Time 510 min: The heating system was switched off, the solution was stirred further until room temperature was reached. The mixture was filtered through a 0.2 μm membrane filter (Sartorius filtration unit). Filtration was carried out within 90 minutes.

A total of 47.82 g of product having a Pt content of 20.75% by weight were obtained with the yield being 99.23% relative to platinum. $^{13}$C-NMR (100.6 MHz, 303 K, DMSO-$d_6$ capillary): δ=168.43; 166.72 ppm. UV-VIS 664 nm (A=0.731); 417 nm (0.763).

Reference Example 2

Production of Platinum Oxalate at 40° C., No Auto-Catalyst

Reference Example 1 was repeated except that the solution was heated for a period of 210 minutes from 23° C. to a temperature of 40° C. The color of the solution turned greenish after 150 minutes at a temperature of 35° C. After 190 minutes, when the temperature was 37° C., the solution began to turn blueish, and after 230 minutes gas production was observed for a period of 65 minutes.

A total of 80.972 g of product having a Pt content of 12.25% by weight were obtained with the yield being 99.19% relative to platinum. $^{13}$C-NMR (151 MHz, 298 K, DMSO-d$_6$ capillary): δ=168.16; 166.67 ppm. UV-VIS 641.05 nm (A=0.342); 417 nm (0.374).

Reference Example 3

Production of Platinum Oxalate at 40° C., No Auto-Catalyst, Oxalic Acid Added in 5 Aliquots A total of 10 g Pt (50 mmol) in the form of 18.01 g H$_2$[Pt(OH)$_6$] were placed in 54.29 ml demineralized water ("VEW") in a 250 ml three-necked round flask.

Time 0 min: The suspension was heated in a water bath from 20° C. to 40° C. over the course of 40 minutes.

Time 40 min: As soon as the temperature of the suspension had reached 40° C., one of five equal aliquots of 2.568 g (20 mmol) oxalic acid dihydrate was added. Neither a color change nor the production of gas was observed. After another 60 minutes, another aliquot of 2.568 g (20 mmol) oxalic acid dihydrate was added. As before, neither a color change nor the production of gas was observed.

Time 160 min: Another 2.568 g (20 mmol) aliquot of oxalic acid dihydrate was added. Ten minutes later, the solution turned greenish. Another 30 minutes later (at 200 minutes), the color of the solution changed from green to turquoise-blue.

Time 220 min: Another 2.568 g (20 mmol) aliquot of oxalic acid dihydrate was added. Ten minutes later, gas production was observed.

Time 280 min: Another 2.568 g (20 mmol) aliquot of oxalic acid dihydrate was added. Gas production continued until the 300 minutes time point. No gas production was observed any longer after this time.

Time 330 min: The heating system was switched off. The solution was stirred further until room temperature was reached. The mixture was filtered through a 0.2 μm membrane filter (Sartorius filtration unit). Filtration was carried out within 30 minutes.

A total of 77.39 g of product having a Pt content of 12.85% by weight were obtained with the yield being 99.45% relative to platinum. $^{13}$C-NMR (151 MHz, 299.6 K, DMSO-d$_6$ capillary): δ=168.16; 166.66 ppm. UV-VIS 664 nm (A=0.373); 417 nm (0.403).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for producing a noble metal oxalate complex, comprising reacting a noble metal precursor with oxalic acid and/or an oxalic acid salt to form a product noble metal oxalate complex, wherein the product noble metal oxalate complex is added to the reaction as an auto-catalyst, and wherein the noble metal precursor and the noble metal oxalate complex are not the same.

2. The method according to claim 1, wherein the reaction is carried out at a temperature below a decomposition temperature of the noble metal oxalate complex.

3. The method according to claim 2, wherein the reaction is carried out at a maximum temperature of 1° C. below the decomposition temperature of the noble metal oxalate complex.

4. The method according to claim 1, wherein the reaction is carried out at a temperature between 0 and 56° C.

5. The method according to claim 1, comprising a first step comprising producing an aqueous solution or suspension of the noble metal precursor and the noble metal oxalate complex, a second step comprising temperature-equilibrating the aqueous solution or suspension to reaction temperature, and a third step comprising adding the oxalic acid and/or oxalic acid salt to the solution or suspension.

6. The method according to claim 1, wherein the amount of added auto-catalyst is $1\times10^{-4}$ to $5\times10^{-2}$ molar equivalents of noble metal relative to the noble metal in the noble metal precursor solution.

7. The method according to claim 1, wherein the oxalic acid and/or oxalic acid salt is selected from the group consisting of oxalic acid, sodium oxalate, ammonium oxalate, potassium oxalate, and mixtures thereof.

8. The method according to claim 1, wherein the noble metal precursor is selected from the group consisting of noble metal oxide hydrate, noble metal nitrate, noble metal acetate, and mixtures thereof.

9. The method according to claim 1, wherein the noble metal is platinum.

10. The method according to claim 9 wherein the platinum precursor is platinum oxide hydrate (platinum-(IV) hydroxoacid) or a salt thereof.

11. The method according to claim 9, wherein the reaction is carried out at a temperature between 30° C. and 45° C.

12. The method according to claim 9, comprising adding 1.8 to 2.8 molar equivalents of oxalic acid relative to the platinum in the platinum precursor.

13. The method according to claim 9, comprising:
   1) producing a suspension of platinum oxide hydrate (platinum-(IV) hydroxoacid) in water;
   2) producing a solution of platinum oxalate complex in water;
   3) combining the suspension 1) and the solution 2) and equilibrating the mixture to a reaction temperature;
   4) adding a first aliquot of 0.4 to 1.4 molar equivalents of oxalic acid relative to the platinum in the platinum oxide hydrate;
   5) adding a second aliquot of 0.1 to 1.4 molar equivalents of oxalic acid relative to the platinum in the platinum oxide hydrate; and
   6) optionally repeating step (5) until a total amount of 1.8 to 2.8 molar equivalents of oxalic acid relative to the platinum in the platinum oxide hydrate have been added.

* * * * *